United States Patent

Lai et al.

[11] Patent Number: 5,945,436
[45] Date of Patent: Aug. 31, 1999

[54] PYRIDYLMETHYL NITRILES, AMIDES AND THIOAMIDES USEFUL AS FUNGICIDES

[75] Inventors: Hoi Kiong Lai, Guelph, Canada; Douglas Irving Relyea, Bethany; Robert Allan Davis, Chesire, both of Conn.

[73] Assignees: Uniroyal Chemical Company, Inc., Middlebury, Conn.; Uniroyal Chemical Co./Cie., Elmira, Canada

[21] Appl. No.: 08/938,535

[22] Filed: Sep. 26, 1997

Related U.S. Application Data

[63] Continuation-in-part of application No. 08/627,749, Apr. 2, 1996, abandoned.

[51] Int. Cl.[6] .......................... A61K 31/44; C07D 213/24
[52] U.S. Cl. ........................... 514/357; 546/330; 546/331; 546/333; 546/337
[58] Field of Search .................... 546/330, 331, 546/333, 337; 514/357

[56] References Cited

U.S. PATENT DOCUMENTS

| | | | |
|---|---|---|---|
| 4,743,603 | 5/1988 | Bulot | 514/235.5 |
| 4,933,339 | 6/1990 | Sharma | 514/235.5 |
| 4,999,357 | 3/1991 | Gadras et al. | 514/277 |
| 5,484,787 | 1/1996 | Shaber et al. | 514/256 |

*Primary Examiner*—Joseph K. McKane
*Attorney, Agent, or Firm*—Daniel Reitenbach

[57] ABSTRACT

Compounds of of the formula

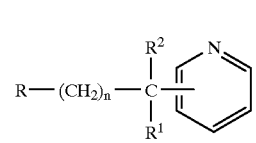

(I)

wherein R is a $C_6$–$C_{10}$ aryl group, optionally substituted with one or more halogen atoms, phenoxy, or, linear or branched, $C_1$–$C_6$ alkyl, $C_1$–$C_6$ alkoxy, $C_1$–$C_6$ haloalkoxy, or $C_1$–$C_6$ haloalkyl; $R^1$ is $C_3$–$C_6$ cycloalkyl or, linear or branched, $C_1$–$C_6$ alkyl, $C_2$–$C_6$ alkenyl, $C_2$–$C_6$ alkynyl, $C_3$–$C_6$ haloalkenyl, $C_2$–$C_8$ alkoxyalkyl or $C_1$–$C_6$ haloalkyl; n is 1, 2 or 3; and $R^2$ is CN, $C(O)NH_2$ or $C(S)NH_2$, or the physiologically acceptable salts thereof with organic and inorganic acids. These compounds are useful as fungicides.

12 Claims, No Drawings

PYRIDYLMETHYL NITRILES, AMIDES AND THIOAMIDES USEFUL AS FUNGICIDES

This is a continuation-in-part of U.S. application Ser. No. 08/627,749, filed on Apr. 2, 1996, now abandoned.

FIELD OF THE INVENTION

The present invention is directed to novel pyridylmethyl nitrites, amides and thioamides useful as fungicides.

BACKGROUND OF THE INVENTION

The control of phytopathogenic fungi is important because fungal growth on plants or plant parts, such fruits, blossoms, foliage, stems, tubers, and roots, inhibits the production of foliage, fruit or seed, and reduces the overall quality of the harvested crop.

Certain pyridyl alkyl nitrites have been described as useful as fungicides. For example, U.S. Pat. No. 4,999,357 describes certain 2-(3-pyridyl)-3-phenoxypropanenitrile derivatives useful as fungicides. U.S. Pat. No. 4,743,603 describes certain fungicidal derivatives of 2-(3-pyridyl)-2-phenylaminoacetic acid. Canadian Patent Application 2,037,162 describes certain heterocyclic acetonitriles with fungicidal activity. U.S. Pat. No. 4,933,339 describes certain fungicidal 2-cyano-2-aryl pyridine compounds.

It is the object of this invention to provide novel pyridylmethyl nitrites and derivatives having fungicidal activity.

SUMMARY OF THE INVENTION

This invention relates to compounds of the formula

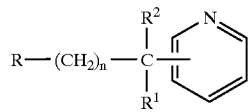

(I)

wherein R is a $C_6-C_{10}$ aryl group, optionally substituted with one or more halogen atoms, phenoxy, or, linear or branched, $C_1-C_6$ alkyl, $C_1-C_6$ alkoxy, $C_1-C_6$ haloalkoxy, or $C_1-C_6$ haloalkyl; $R^1$ is $C_3-C_6$ cycloalkyl or, linear or branched, $C_1-C_8$ alkyl, $C_2-C_6$ alkenyl, $C_2-C_6$ alkynyl, $C_3-C_6$ haloalkenyl, $C_2-C_8$ alkoxyalkyl, or $C_1-C_6$ haloalkyl; n is 1, 2 or 3; and $R^2$ is CN, $C(O)NH_2$ or $C(S)NH_2$, or the physiologically acceptable salts thereof with organic and inorganic acids. These compounds are useful as fungicides.

The present invention is also related to fungicidal compositions comprising a fungicidally effective amount at least one compound of formula I above.

The present invention is additionally related to a process for controlling undesirable fungi which comprises applying a fungicidally effective amount of at least one compound or composition of the present invention, to a locus to be protected.

DETAILED DESCRIPTION OF THE INVENTION

Preferred compounds of this invention are the compounds of formula I having the formula

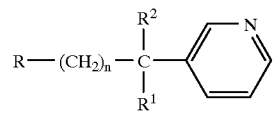

(IA)

wherein R, $R^1$, $R^2$ and n are as described above, and, more preferably, wherein R is naphthyl or phenyl optionally substituted with one or more halogen atoms, or, linear or branched, $C_1-C_4$ alkyl, $C_1-C_4$ alkoxy or $C_1-C_4$ haloalkyl; $R^1$ is $C_3-C_6$ cycloalkyl or, linear or branched, $C_2-C_4$ alkyl, $C_2-C_4$ haloalkyl, $C_2-C_4$ alkenyl or $C_2-C_4$ alkynyl; $R^2$ is a cyano group; and n is 2 or 3.

Particularly preferred are those compounds of formula IA wherein R is phenyl optionally substituted with one or more halogen atoms, trifluoromethyl, or, linear or branched, $C_1-C_4$ alkyl or $C_1-C_4$ alkoxy.

Compounds of formula (I) can be prepared according to the following reaction scheme:

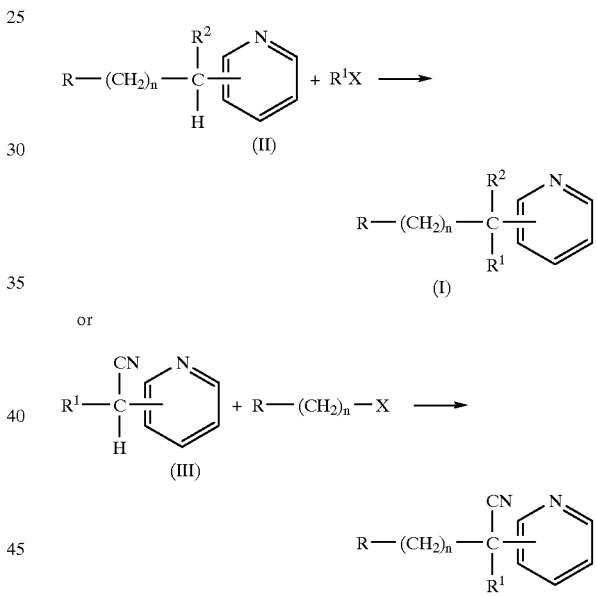

wherein X is a leaving group such as chlorine or bromine atom and R, $R^1$, $R^2$ and n are as previously defined. Accordingly, an aralkyl substituted pyridine is reacted with an equal molar of the halide in the presence of a base such as sodium amide in an inert solvent, preferably tetrahydrofuran, at a temperature between −78° C. to room temperature. The resulting reaction mixture is then neutralized with an acid prior to the purification of the compound of formula I by column chromatography.

Alternatively, compounds of formula I can be prepared by reacting a substituted aliphatic pyridine with an aralkyl halide under analogous conditions as described above.

The intermediate aralkyl substituted pyridine (II) can be prepared by reaction of pyridylmethyl nitrile with an equal molar of appropriate aralkyl halide. The reaction is carried out in the presence of a base such as sodium amide, in an inert solvent, preferably tetrahydrofuran.

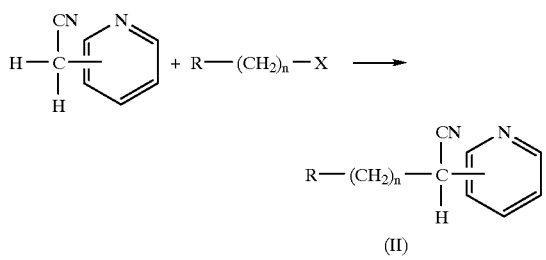

(II)

The intermediate aliphatic pyridine (III) can be prepared by reaction of a pyridylacetonitrile with an equal molar of an appropriate halide under analogous conditions as described above.

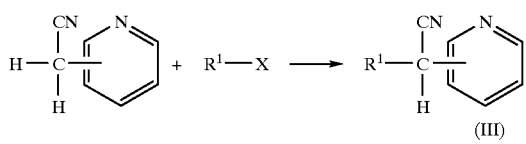

(III)

Pyridylacetonitriles and halides useful in the preparation of the compounds of this invention are commercially available.

Compounds of formula I wherein $R^2$ is carboxamide ($CONH_2$) can be prepared as described in the Journal of Organic Chemistry 59: 284 (1994).

Compounds of formula I in which $R^2$ is thioamide ($CSNH_2$) can be prepared by treating the corresponding compound of formula I in which $R^2$ is CN, in an inert solvent preferably toluene with a steady stream of hydrogen sulfide gas, catalyzed by the presence of a secondary amine preferably diethylamine. The reaction is conducted between room temperature to about 45° C.

Physiologically acceptable salts can be prepared using methods known in the art, for example, by dissolving a compound of formula I in suitable inert solvent and adding an acid such as hydrochloric acid, and can be isolated using known methods, e.g., by filtration, and, if appropriate, purified by washing with an inert organic solvent.

In the process of this invention, a fungicidally effective amount of the compound of formula I is applied to the locus under attack by fungi. A fungicidally effective amount of the compound of formula I can be applied to the foliage of the plants to be protected from phytopathogenic fungi. This procedure is referred as the foliage method. The compound can be applied to the foliage in a concentration of about 0.125 to about 10 kilograms per hectare (kg/ha), preferably from about 0.125 to about 5.0 kg/ha.

Alternatively, a fungicidally effective amount of the compound of formula I can be applied to the soil in which the plants to be protected are grown. This procedure is referred to as the systemic method. The compound can be applied to the soil at a concentration of about 10 to about 500 mg/L. The exact dosage will depend on the fungi to be controlled and the particular plants to be protected.

Either the foliage method or the systemic method can be utilized prior to or after, fungal infection.

In another alternative method, the compound of formula I can be applied to seeds as a coating. In this method, the appropriate concentration of the compound is in the range of between about 5 and about 400 grams of compound per 100 kg. of seed.

The fungicidal compositions of the present invention comprise a fungicidally effective amount of a compound of formula I and a suitable carrier. A "suitable carrier" for the purposes of this invention, is any solid or liquid which is biologically, chemically, and physically compatible with the compound of formula I.

A suitable carrier useful in the fungicidal compositions of this invention, can be a finely divided or granular organic or inorganic inert material. Useful inert carriers include attapulgate clay, sand, vermiculite, corncobs, activated carbon and mineral silicates such as mica, talc, pyrophyllite and clays.

The suitable carrier can also be a solvent. The compound of formula I is dissolved in a suitable solvent, or mixture of solvents, which acts as the carrier. Useful solvents include acetone, methanol, ispropanol, t-butyl alcohol, cyclohexanone, toluene, xylene, dioxane, dimethylformamide, dimethylsulfoxide, ethylene dichloride, diacetone alcohol, and N-methylpyrrolidone.

The compound of formula I can also be dissolved in a suitable solvent or mixture of solvents, together with a surface active agent, to produce an emulsion. Examples of useful surface active agents can be found, e.g., in *McCutcheon's Detergents and Emulsifiers* (Allured Publishing Corp., Ridgewood, N.J., 1970); U.S. Pat. No. 2,514,916; and U.S. Pat. No. 2,547,734. The surface active agents can be anionic, non-ionic or cationic.

The suitable carrier can be a dispersant comprising a suitable solvent, a suitable surface active agent, and water. The compound of formula I can be dissolved in the solvent to form a solution and the solution can then be dispersed in the water with the aid of the surface active agent.

The compound of formula I can also be premixed with an inert solid carrier which is added to a surface active agent and water to provide another form of dispersion type carrier.

The composition of this invention can take the form of dust, granules or a paste of a wettable powder. The compound of formula I is admixed with an inert solid carrier to form a solid composition. To form a powder, the solid inert carrier, such as a mineral silicate, is provided in powder form. The solid composition can be made wettable by the addition of a surface active agent.

Finally, the suitable carrier can be an aerosol. To prepare an aerosol composition, the compound of formula I is initially dissolved in a volatile first solvent. The resultant solution is then admixed with a highly volatile solvent, a liquid aerosol carrier. A highly volatile solvent is liquid only under elevated pressure. At ordinary temperatures and at atmospheric pressure, the highly volatile solvent is a gas. The liquid aerosol carrier is a highly volatile solvent but the volatile first solvent is not a highly volatile solvent.

The aerosol carrier can itself be pesticidally active. For example, the aerosol carrier can be an insecticide, a herbicide, a bactericide, or the like.

Particularly preferred are the compositions of this invention comprising solvents and emulsions.

The following examples are provided to illustrate the present invention.

EXAMPLE 1

Preparation of α-(2-phenylethyl)-3-pyridineacetonitrile (This example illustrates the preparation of an intermediate aralkyl pyridine of formula II.)

A solution of 3-pyridylacetonitrile (23 g) in tetrahydrofuran (75 ml) was added dropwise to a stirred suspension of sodium amide (8 g) in tetrahydrofuran (175 ml) under a nitrogen atmosphere at 0° C. After complete addition of the solution, the resultant mixture was stirred at 0–10° C. for 1 hour, then cooled to −35° C. and a solution of 2-(bromoethyl)benzene (36 g) in tetrahydrofuran (100 ml) was added dropwise over 30 minutes. The resultant new mixture was stirred between −35° C. to ambient temperature overnight, then quenched with water and neutralized with 10% hydrochloric acid. After the removal of of tetrahydrofuran, the residue was dissolved in methylene chloride and washed with saturated sodium bicarbonate solution. The organic extract was then dried over magnesium sulfate, filtered and evaporated to give an oil. The oil was then distilled to provide 30 g of α-(2-phenylethyl)-3-pyridineacetonitrile, b.p.=170–173° C./0.5 mmHg.

EXAMPLE 2

Preparation of (α-propyl)-3-pyridineacetonitrile (This example illustrates the preparation of an intermediate aliphatic pyridine of formula III.)

Using the procedure described in Example 1 except that iodopropane replaced the 2-(bromoethyl)benzene, 3-pyridylacetontrile (25 g) was reacted with iodopropane (35.6 g) in the presence of sodium amide (9.6 g) in tetrahydrofuran (300 ml) to produce 23 g of (α-propyl)-3-pyridineacetonitrile, b.p.=105° C./0.5 mmHg.

EXAMPLE 3

Preparation of 4-fluoro-α-(2-propenyl)-α-(3-pyridinyl) benzenebutanenitrile (Compound #9)

A solution of α-[2-(4-fluorophenyl)ethyl]-3-pyridineacetonitrile (4 g) in tetrahydrofuran (30 ml) was added dropwise, under nitrogen atmosphere, to a stirred suspension of sodium amide (0.8 g) at 0° C. After complete addition (~20 minutes) the resultant mixture was stirred at 0° C. for 1 hour followed by 1 hour at room temperature. The mixture was then cooled to −40° C. and treated with dropwise addition of a solution of allyl bromide (2 g) in tetrahydrofuran (30 ml) to produce a reaction mixture. The reaction mixture was allowed to warm up to room temperature overnight, then neutralized with 10% hydrochloric acid and worked up by extraction with methylene chloride to produce a crude reaction product. The crude reaction product was then chromatographed on a silica gel column and eluted with 25% ethyl acetate in hexanes to give 3.7 g of 4-fluoro-α-(2-propenyl)-α-(3-pyridinyl)benzenebutanenitrile. The structure was confirmed by NMR spectroscopy.

EXAMPLE 4

Preparation of 2-chloro-α-propyl-(3-pyridinyl)benzene pentanenitrile (Compound #15)

Using the procedure described in Example 3 above, (α-propyl)-3-pyridineacetonitrile prepared as described in Example 2 above,(4.6 g) and 3-(2-chlorophenyl)-1-brompopropane (6.7 g) were reacted together in the presence of sodium amide (1.3 g) in tetrahydrofuran (100 ml) to produce 3.5 g of 2-chloro-α-propyl-(3-pyridinyl)benzene pentanenitrile. After purification by silica gel chromatography the structure was confirmed by NMR spectroscopy.

EXAMPLE 5

Preparation of α-butyl-4-ethoxy-α-(3-pyridinyl)-benzenebutanenitrile hydrochloride (Compound #42)

A solution of α-butyl-4-ethoxy-α-(3-pyridinyl)-benzenebutanenitrile (2.5 g) in diethylether (125 ml) was cooled in an ice-water bath. A steady stream of hydrogen gas was bubbled through the solution until production of precipitation ceased. The solvent was then removed under reduced pressure to give 2.5 g of α-butyl-4-ethoxy-α-(3-pyridinyl)-benzenebutanenitrile hydrochloride which was hygroscopic and was kept free of moisture prior to the determination of its NMR spectrum.

EXAMPLE 6

Preparation of α-(2-phenylethyl)-α-(2-propynyl)-3-pyridinethanethioamide (Compound #61)

A slow, steady stream of hydrogen sulfide was passed into a toluene solution (75 ml) of α-(2-phenylethyl)-α-(2-propyl)-3-pyridineacetonitrile (3.5 g) in the presence of diethylamine (1 ml). More diethylamine was added at the end of 1 hour (0.5 ml) and 3 hours (0.5 ml). The resultant reaction mixture was then evaporated to dryness and the residue dissolved in methylene chloride and washed with saturated sodium bicarbonate and water. After washing, the remaining organic extract was dried over sodium sulfate and worked up to give a solid. Recrystallization with hexanes produced α-(2-phenylethyl)-α-(2-propynyl)-3-pyridinethanethioamide with a melting point of 73–74° C.

EXAMPLE 7

Preparation of α-[4-fluorophenyl)ethyl]-α-pentyl-3-pyridineacetamide (Compound #62)

To a solution of 4-fluoro-α-pentyl-α-(3-pyridinyl)-benzenebutanenitrile (3.5 g) in methylene chloride (25 ml) were added successively hydrogen peroxide (15.9 g of 35% grade), n-butylammonium hydrogen sulfate (0.78 g) and an aqueous sodium hydroxide solution (4.0 ml of 20% strength). The resultant reaction mixture was then refluxed for 2.5 hour and then extracted with methylene chloride. The organic extract was washed with saturated sodium chloride solution, dried over magnesium sulfate and worked up in the usual manner to give a sticky solid. This solid was then heated in diethylether and the solid collected by suction filtration and identified by NMR to be α-[4-fluorophenyl)ethyl]-α-pentyl-3-pyridineacetamide, m.p.=170° C., yield=1 g.

The filtrate upon evaporation was found to contain unreacted 4-fluoro-α-pentyl-α-(3-pyridinyl)-benzenebutanenitrile.

EXAMPLE 8

Preparation of Compounds 1–81

Additional compounds of formula I were prepared in accordance with the procedures described in Examples 1 through 7. These compounds, including their characterizing melting points or NMR data, are summarized in Table I below.

TABLE I

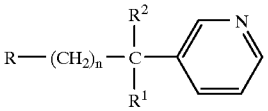

| No. | R | n | R² | R¹ | HNMR - Taken in deuterated chloroform unless otherwise specified. |
|---|---|---|---|---|---|
| 1 | phenyl | 2 | CN | $CH_3(CH_2)_2-$ | δ: 0.91(3H, t); 1.15, 1.50(2m, 2H); 1.85–2.45(4H, m); 2.80(2H, m); 7.08–7.28(5H, m); 7.38(1H, m); 7.77(1H, m); 8.60(1H, m); 8.74(1H, d) |
| 2 | " | " | " | $CH_3(CH_2)_6-$ | δ: 0.85(3H, t); 1.22(10H, b); 1.85–2.45(4H, m); 2.79(2H, m); 7.38(1H, m); 7.78(1H, m); 8.61(1H, m); 8.73(1H, d) |
| 3 | " | " | " | $CH_3(CH_2)_4-$ | δ: 0.83(3H, t); 1.25(6H, b); 1.90–2.90(4H, m); 7.08–7.26(5H, m); 7.38(1H, m); 7.80(1H, m); 8.60(1H, m); 8.74(1H, d) |
| 4 | " | " | " | $CH{\equiv}CCH_2-$ | δ: 8.6–8.9(2H, m); 7–7.80(1H, m); 7.25–7.45(1H, m); 7.1–7.2(5H, m); 2.9(2H, d); 2.3–2.7(4H, m); 2.15(1H, t) |
| 5 | " | " | " | $CH_2{=}CHCH_2-$ | δ: 8.7–8.8(2H, m); 7.6–7.9(1H, m); 7.25–7.45(1H, m); 7.0–7.3(5H, m); 5.5–6.0(1H, m); 5.0–5.24(2H, bq); 2.8(2H, d); 2.0–2.6(4H, m) |
| 6 | " | " | " | $CH_3OCH_2-$ | δ: 8.5–8.8(2H, m); 7.6–7.9(1H, m); 7.2–7.4(1H, m); 7.0–7.3(5H, m); 3.6(2H, s); 3.3(3H, s); 2.1–2.8(4H, m) |
| 7 | " | " | " | $(CH_3)_2CHCH_2-$ | δ: 8.86–8.8(2H, m); 7.7–7.9(1H, m); 7.25–7.45(1H, m); 7.0–7.3(5H, m); 2.15(2H, d); 2.0–2.8(4H, m); 1.2–2.0(1H, m); 0.9(3H, d); 0.8(3H, d) |
| 8 | " | " | " | $(CH_3)_2C{=}CHCH_2-$ | δ: 8.55–8.75(2H, m); 7.7–7.9(1H, m); 7.2–7.4(1H, m); 7.0–7.3(5H, m); 5.1(1H, t); 2.2–2.9(6H, m); 1.65(3H, s); 1.5(3H, s) |
| 9 | 4-fluoropheyl | 2 | CN | $CH_2{=}CHCH_2-$ | δ: 8.6–8.8(2H, m); 7.7–7.9(1H, m); 7.25–7.4(1H, m); 6.9–7.1(4H, m); 5.4–6.1(1H, m); 4.95–5.25(2H, 6q); 2.8(2H, d); 2.0–2.5(4H, m) |
| 10 | " | " | " | $CH_3(CH_2)_2-$ | δ: 8.6–8.8(2H, m); 7.7–7.9(1H, m); 7.25–7.35(1H, m); 6.9–7.2(4H, m); 1.8–3.0(6H, m); 1.2–1.6(2H, m); 0.7–1.0(3H, m) |
| 11 | " | " | " | $CH_3(CH_2)_3-$ | δ: 8.5–8.75(2H, m); 7.65–7.85(1H, m); 7.2–7.4(1H, m); 6.8–7.0(4H, m); 1.8–2.9(6H, m); 1.2–1.7(4H, m); 0.8–1.0(3H, m) |
| 12 | 4-chlorophenyl | 3 | " | $CH_3(CH_2)_2-$ | δ: 8.6–8.8(2H, m); 7.7–7.9(1H, m); 7.2–7.4(1H, m); 7.1(4H, 1.8–2.9(6H, m); 1.2–1.7(4H, m); 0.8–1.0(3H, m) |
| 13 | " | " | " | $CH_3(CH_2)_3-$ | δ: 8.6–8.8(2H, m); 7.7–7.9(1H, m); 7.25–7.45(1H, m); 7.15(4H, q); 1.8–2.8(6H, m); 1.1–1.5(6H, m); 0.8(3H, m) |
| 14 | 4-t-butylphenyl | 1 | " | $CH_3(CH_2)_2-$ | δ: 8.55—8.75(2H, m); 7.5–7.8(1H, m); 7.2–7.4(1H, m); 7.15(4H, q); 3.2(2H, d); 2.2(2H, t); 1.3(9H, s); 1.2–1.4(2H, m); 0.8–1.1(3H, m) |
| 15 | 2-chlorophenyl | 3 | " | " | δ: 8.5–8.75(2H, m); 7.6–7.8(1H, m); 7.2–7.4(1H, m); 6.9–7.2(4H, m); 2.7(2H, bt); 1.1–2.2(8H, m); 0.7–1.0(3H, m) |
| 16 | 4-t-butylphenyl | 1 | " | $CH_3(CH_2)_5-$ | δ: 8.5–8.7(2H, m); 7.5–7.7(1H, m); 7.2–7.4(1H, m); 7.1(4H, q); 3.15(2H, bs); 1.9–2.0(2H, M); 1.2(9H, s); 1.0–1.4(8H, m); 0.7–0.9 (3H, m) |
| 17 | 4-phenoxy-phenyl | 1 | CN | $CH_3(CH_2)_2-$ | δ: 8.5–8.7(2H, m); 7.5–7.7(1H, m); 7.2–7.4(1H, m); 6.6–7.3(9H, m); 3.2(2H, D); 1.8–2.2(2H, M); 1.2–1.5(2H, m); 0.8–1.1(3H, m) |

TABLE I-continued

| No. | R | n | $R^2$ | $R^1$ | HNMR - Taken in deuterated chloroform unless otherwise specified. |
|---|---|---|---|---|---|
| 18 | 4-t-butylphenyl | " | " | $CH_2$=$CHCH_2$— | δ: 8.5–8.7(2H, m); 7.5–7.7(1H, m); 7.2–7.4(1H, m); 7.05(4H, q); 5.6–6.0(1H, m); 4.9–5.2(2H, q); 3.16(2H, bs); 2.8(2H, bd); 1.2(9H, s) |
| 19 | " | " | " | $CH_3(CH_2)_3$— | δ: 8.6–8.8(2H, m); 7.6–7.8(1H, m); 7.2–7.4(1H, m); 7.15(4H, q); 3.2(2H, bs); 2.0–2.2(2H, m); 1.3(9H, s); 1.1–1.4(4H, m); 0.95(3H, bt) |
| 20 | naphthyl | " | " | $CH_3(CH_2)_2$— | δ: 8.4–8.7(2H, m); 7.0–7.8(1H, m); 3.60(2H, d); 2.0–2.2(2H, m); 1.1–1.5(2H, m); 0.9(3H, t) |

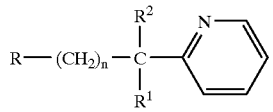

| No. | R | n | $R^2$ | $R^1$ | HNMR - Taken in deuterated chloroform unless otherwise specified. |
|---|---|---|---|---|---|
| 21 | naphthyl | 1 | CN | $CH_3(CH_2)_3$— | δ: 8.6–8.8(1H, m); 7.6–7.8(2H, m); 7.2–7.4(1H, m); 7.15(5H, s); 1.9–2.8(6H, m); 1.1–1.4(4H, m); 0.85(3H, bt) |
| 22 | " | " | " | $CH_2$=$CHCH_2$— | δ: 8.55–8.75(1H, m); 7.6–7.8(2H, m); 7.2–7.4(1H, m); 7.2(5H, S); 5.4–5.9(1H, m); 4.9–5.2(2H, q); 2.8(2H, bd); 2.2–2.6(4H, m) |
| 23 | " | " | " | $CH_3(CH_2)_6$ | δ: 8.6–8.8(1H, m); 7.7–7.8(2H, m); 7.2–7.4(1H, m); 7.18(5H, m); 1.8–2.7(6H, m); 1.1–1.3(10H, m); 0.7–0.9(3H, bt) |
| 24 | " | " | " | $(CH_3)_2C$=$CHCH_2$— | δ: 8.6–8.8(1H, m); 7.5–7.8(2H, m); 7.2–7.4(1H, m); 7.2(5H, m); 5.0–5.3(1H, bt); 2.8(2H, bd); 2.1–2.7(4H, m); 1.76(3H, s); 1.5(3H, s) |

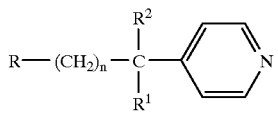

| No. | R | n | $R^2$ | $R^1$ | HNMR - Taken in deuterated chloroform unless otherwise specified. |
|---|---|---|---|---|---|
| 25 | phenyl | 2 | CN | $CH_3(CH_2)_2$— | δ: 8.66(2H, d); 7.35(2H, d); 7.6(5H, bs); 1.8–2.8(6H, m); 1.2–1.5(2H, m); 0.8–1.0(3H, bt) |
| 26 | " | " | " | $CH_3(CH_2)_3$— | δ: 8.7(2H, d); 7.35(2H, d); 7.2(5H, bs); 1.8–2.8(6H, m); 1.1–1.5(4H, m); 0.7–0.9(3H, bt) |

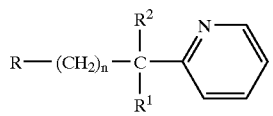

| No. | R | n | $R^2$ | $R^1$ | HNMR - Taken in deuterated chloroform unless otherwise specified. |
|---|---|---|---|---|---|
| 27 | 4-methoxy-phenyl | 2 | CN | $CH_3(CH_2)_3$— | δ: 8.5–8.8(2H, m); 7.7–7.9(1H, m); 7.2–7.4(1H, m); 6.9(4H, q); 3.7(3H, s); 2.2–2.9(4H, m); 1.2–2.0(4H, m); 0.7–1.1(3H, m) |
| 28 | " | " | " | $CH_2$=$CHCH_2$— | δ: 8.7–8.9(2H, m); 7.8–8.0(1H, m); 7.4–7.6(1H, m); 7.2(4H, q); 5.8–6.0(1H, m); 5.0–5.2(2H, q); 3.8(3H, s); 2.9(2H, d); 2.2–2.5(4H, m) |
| 29 | " | " | " | $(CH_3)_2CHCH_2$— | δ: 8.6–8.8(2H, m); 7.7–7.9(1H, m); 7.2–7.4(1H, m); 6.9(4H, q); 3.75(3H, s); 2.2(2H, d); 2.0–2.4(4H, m); 1.2–1.8(1H, m); 0.85(3H, d); 0.75(3H, s) |
| 30 | " | " | " | $CH_3(CH_2)_4$— | δ: 8.6–8.8(2H, m); 7.7–7.9(1H, m); 7.25–7.45(1H, m); 6.9(4H, q); |

TABLE I-continued

| No. | R | n | R² | R¹ | HNMR - Taken in deuterated chloroform unless otherwise specified. |
|---|---|---|---|---|---|
| 31 | " | " | " | CH₃(CH₂)₃— | δ: 3.75(3H, s); 1.8–2.8(6H, m); 1.1–1.5(6H, m); 0.7–0.9(3H, m) 8.6–8.8(2H, m); 7.75–7.95(1H, m); 7.2–7.4(1H, m); 6.9(4H, q); 3.75(3H, s); 1.8–2.8(6H, m); 1.1–1.5(4H, m); 0.85(3H, t) |
| 32 | 4-chlorophenyl | 3 | " | (C₃H₅)CH₂— | δ: 8.5–8.8(2H, m); 7.7–7.9(1H, m); 7.15–7.35(1H, m); 7.05(4H, q); 2.4–2.7(2H, bt); 1.8(2H, bd); 1.0–2.1(5H, m); 0.3–0.6(4H, m) |

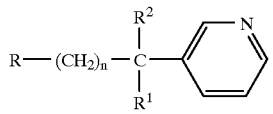

| No. | R | n | R² | R¹ | HNMR - Taken in deuterated chloroform unless otherwise specified. |
|---|---|---|---|---|---|
| 33 | 4-methylphenyl | 2 | CN | CH=CHCH₂— | δ: 8.6–8.8(2H, m); 7.7–7.9(1H, m); 7.2–7.4(1H, m); 7.15(4H, q); 5.6–5.8(1H, m); 5.1–5.2(2H, q); 2.65–2.85(2H, m); 2.3(3H, s); 2.2–2.4(4H, m) |
| 34 | " | " | " | CH₃(CH₂)₃— | δ: 8.5–8.8(2H, m); 7.75–7.85(1H, m); 7.3–7.4(1H, m); 7.05(4H, q); 1.9–2.8(6H, m); 2.3(3H, s); 1.1–1.5(4H, m); 0.85(3H, t) |
| 35 | 4-ethoxyphenyl | " | " | " | δ: 8.4–8.6(2H, m); 7.5–7.8(1H, m); 7.1–7.3(1H, m); 6.8(4H, q); 3.8(2H, q); 1.7–2.8(6H, m); 1.3(3H, t); 0.9–1.3(4H, m); 0.75(3H, s) |
| 36 | 4-methoxy-phenyl | " | " | CH₃(CH₂)₅— | δ: 8.7–8.9(2H, m); 7.7–7.9(1H, m); 7.3–7.5(1H, m); 6.8–7.25(4H, q); 3.8(3H, s); 1.8–2.8(6H, m); 1.2–1.5(8H, m); 0.8–1.0(3H, m) |
| 37 | " | " | " | (C₃H₅)—CH₂— | δ: 8.5–8.8(2H, m); 7.7–7.9(1H, m); 7.2–7.4(1H, m); 6.9(4H, q); 3.7(3H, s); 1.5–1.8(1H, m); 1.8–2.4(6H, m); 0.3–0.6(4H, m) |
| 38 | " | " | " | CH≡CCH₂— | δ: 8.5–8.8(2H, m); 7.7–7.9(1H, m); 7.2–7.4(1H, m); 6.9(4H, q); 3.75(3H, s); 2.9(2H, d); 2.3–2.6(4H, m); 2.15(1H, t) |
| 39 | 4-fluorophenyl | " | " | (CH₃)₂CHCH₂— | δ: 8.5–8.75(2H, m); 7.7–7.9(1H, m); 7.2–7.4(1H, m); 6.8–7.0(4H, m); 2.2–2.8(4H, m); 2.1(2H, d); 1.3–1.8(1H, m); 0.85(3H, d); 0.75(3H, d) |
| 40 | 4-ethoxyphenyl | " | " | CH₂=CHCH₂— | δ: 8.5–8.8(2H, m); 7.7–7.9(1H, m); 7.2–7.4(1H, m); 6.9(4H, q); 5.4–6.0(1H, m); 5.0–5.2(2H, q); 3.95(2H, q); 2.8(2H, d); 2.1–2.5(4H, m); 1.4(3H, t) |
| 41 | 4-fluorophenyl | 2 | CN | CH≡CHCH₂— | δ: 8.5–8.8(2H, m); 7.7–7.9(1H, m); 6.8–7.1(4H, m); 2.9(2H, d); 2.3–2.7(4H, m); 2.2(1H, t) |
| 42* | 4-ethoxyphenyl | " | " | CH₃(CH₂)₃— | δ(DMSOd₆) 13.0(1H, bs); 8.9–9.1 (2H, m); 8.6–8.8(1H, m); 8.0–8.2(1H, m); 6.95(4H, q); 4.05(2H, q); 2.1–2.6(6H, m); 1.3(3H, t); 1.1–1.3(4H, m); 0.8(3H, t) |
| 43 | " | " | " | (CH₃)₂CHCH₂— | δ: 8.5–8.8(2H, m); 7.7–7.9(1H, m); 7.2–7.4(1H, m); 6.9(4H, q); 3.95(2H, q); 2.2–2.8(4H, m); 2.1(2H, d); 1.5–1.9(1H, m); 1.35(3H, t); 0.9(3H, d); 0.8(3H, d) |
| 44 | " | " | " | CH₃(CH₂)₅— | δ: 8.6–8.8(2H, m); 7.8–7.9(1H, m); 7.2–7.4(1H, m); 6.9(4H, q); 4.0(2H, q); 1.8–2.8(6H, m); 1.4(3H, t); 1.1–1.3(8H, m); 0.7–1.0(3H, m) |
| 45 | 4-fluorophenyl | " | " | " | δ: 8.7–8.9(2H, m); 7.7–7.9(1H, m); 7.2–7.4(1H, m); 6.9–7.1(4H, m); 1.9–2.9(6H, m); 1.1–1.5(8H, m); 0.8–1.0(3H, m) |
| 46 | 4-ethoxypehnyl | " | " | CH₃(CH₂)₂— | δ: 8.6–8.8(2H, m); 7.7–7.9(1H, m); 7.2–7.4(1H, m); 6.9(4H, q); 4.0(2H, q); |

TABLE I-continued

| | | | | | | |
|---|---|---|---|---|---|---|
| | | | | | | 1.7–2.8(8H, m); 1.35(3H, t); 0.8–1.1(3H, m); |
| 47 | 4-fluorophenyl | " | " | (CH₃)₂C=CHCH₂— | δ: | 8.5–8.8(2H, m); 7.7–7.9(1H, m); 7.2–7.4(1H, m); 6.8–7.1(4H, m); 5.1(1H, bt); 2.7(2H, bd); 2.1–2.6(4H, m); 1.62(3H, s); 1.48(3H, s) |
| 48 | 4-methoxy-phenyl | 2 | CN | (CH₃)₂C=CHCH₂— | δ: | 8.55–8.75(2H, m); 7.7–7.9(1H, m); 7.2–7.4(1H, m); 6.9(4H, q); 5.15(1H, t); 3.7(3H, s); 2.7(2H, d); 1.8–2.5(4H, m); 1.76(3H, s); 1.5(3H, s) |
| 49 | 4-fluorophenyl | " | " | (CH₃)₂CHCH₂CH₂— | δ: | 8.5–8.7(2H, m); 7.6–7.8(1H, m); 7.2–7,.4(1H, m); 6.8–7.0(4H, m); 1.8–2.8(1H+4H, m); 1.1–1.5(4H, m); 0.6–0.8(6H, m) |
| 50 | 4-methoxy-phenyl | " | " | CH₃OCH₂— | δ: | 8.5–8.8(2H, m); 7.7–7.9(1H, m); 7.2–7.4(1H, m); 6.8–7.1(4H, m); 3.7(2H, s); 3.68(3H, s); 3.3(3H, s); 2.1–2.8(4H, m) |
| 51 | 4-fluorophenyl | " | " | " | δ: | 8.7–8.9(2H, m); 7.7–7.9(1H, m); 7.2–7.4(1H, m); 6.8–7.1(4H, m); 3.7(2H, s); 3.34(2H, s), 3.34(3H, s); 2.2–2.8(4H, m) |
| 52 | " | " | " | CF₃CH₂— | δ: | 8.7–8.9(2H, m); 7.8–8.0(1H, m); 7.3–7.5(1H, m); 6.8–7.1(4H, m); 2.3–3.2(6H, m) |
| 53 | " | " | " | FCH₂CH₂— | δ: | 8.65–8.85(2H, m); 7.8–7.9(1H, m); 7.2–7.5(1H, m); 6.8–7.1(4H, m): 4.95(1H, t); 4.15(1H, t); 2.1–2.9(6H, m) |
| 54 | 4-butoxyphenyl | " | " | CH₃(CH₂)₃— | δ: | 8.65–8.75(2H, m); 7.7–7.9(1H, m); 7.2–7.4(1H, m); 6.9(4H, q); 3.9(2H, t); 1.1–2.8(14H, m); 0.7–1.0(6H, t+t) |
| 55 | 4-fluorophenyl | " | " | (CH₃)₂CHCH₂CH₂— | δ: | 9.1–9.3(2H, m); 8.7–8.9(1H, m); 8.2–8.4(1H, m); 6.8–7.3(4H, m); 2.0–2.8(6H, m); 1.1–1.6(1H+2H, m); 0.9(3H, bs); 0.85(3H, bs) |
| 56 | 4-butoxyphenyl | 2 | CN | CH₂=CHCH₂— | δ: | 8.5–8.8(2H, m); 7.6–7.8(1H, m); 7.15–7.35(1H, m); 6.84(4H, q); 5.3–5.9(1H, m); 4.9–5.1(2H, q); 3.8(2H, t); 2.6(2H, bd); 2.0–2.3(4H, bt); 1.2–1.6(4H, m); 0.7–1.9(6H, t+t) |
| 57 | " | " | " | CH₃(CH₂)₂— | δ: | 8.5–8.8(2H, m); 7.7–7.9(1H, m); 7.2–7.4(1H, m); 6.85(4H, q); 3.8(2H, t); 2.1–2.8(6H, m); 1.2–1.8(6H, m); 0.85(6H, bt) |
| 58 | " | " | " | (CH₃)₂CHCH₂— | δ: | 8.5–8.8(2H, m); 7.7–7.9(1H, m); 7.2–7.4(1H, m); 6.85(4H, q); 3.85(2H, t); 2.1–2.8(4H, m); 2.0(2H, d); 1.2–1.7(1H+2H, m); 0.90(3H, d): 0.80(3H, d) |
| 59 | 4-fluorophenyl | " | " | CH₃CH=CH—CH₂— | δ: | 8.6–8.8(2H, m); 7.7–7.9(1H, m); 7.2–7.4(1H, m); 6.8–7.1(4H, q); 5.3–5.5(2H, m); 2.2–2.8(6H, m); 1.6(3H, d) |
| 60 | " | " | " | CH₃(CH₂)₄— | δ: | 8.6–8.8(2H, m); 7.7–7.9(1H, m); 7.2–7.4(1H, m); 6.8–7.0(4H, m); 1.8–2.7(6H, m); 1.1–1.4(6H, m); 0.85(3H, bt) |
| 61 | " | " | —C(=S)—NH₂ | CH≡CCH₂— | | m.p. = 73–74° C. |
| 62 | " | " | —C(=O)—NH₂ | CH₃(CH₂)₄— | | m.p. = 175° C. |
| 63 | 2-methoxy-phenyl | 3 | CN | CH₃(CH₂)CH₂— | δ: | 8.5–8.7(2H, m); 7.55–7.75(1H, m); 7.2–7.4(1H, m); 6.7–7.1(4H, m); 3.7(3H, s); 2.5(2H. t); 1.6–2.1(4H, m); 1.1–1.4(6H, m); 0.85(3H, bt) |

TABLE I-continued

| | | | | | |
|---|---|---|---|---|---|
| 64 | 4-fluorophenyl | 2 | CN | FCH$_2$(CH$_2$)$_2$— | δ: 8.6–8.8(2H, m); 7.7–7.9(1H, m); 7.2–7.4(1H, m); 6.8–7.1(4H, m); 4.75(1H, t); 3.9(1H, t); 1.9–2.8(6H, m); 1.4–1.6(2H, m) |
| 65 | " | " | " | CH$_2$=CCl—CH$_2$— | δ: 8.6–8.8(2H, m); 7.7–7.9(1H, m); 7.3–7.5(1H, m); 6.8–7.1(4H, m); 5.25(2H, d+d); 2.3–3.1(6H, m) |
| 66 | 2-fluorophenyl | " | " | FCH$_2$(CH$_2$)$_2$— | δ: 8.6–8.8(2H, m); 7.7–7.9(1H, m); 7.2–7.4(1H, m); 6.9–7.2(4H, m); 4.8(1H, t); 4.0(1H, t); 2.5–3.1(2H, m); 2.0–2.5(4H, m); 1.3–1.6(2H, m) |
| 67 | " | " | " | CH$_2$=CH—CH$_2$— | δ: 8.6–8.8(2H, m; 7.8–7.9(1H, m); 7.2–7.4(1H, m); 6.9–7.2(4H, m); 5.4–5.9(1H, m); 4.95–5.20(2H, q); 2.7(2H, bd); 2.1–2.6(4H, m) |
| 68 | 4-fluoroethoxy-phenyl | " | " | CH$_3$(CH$_2$)$_3$— | δ: 8.5–8.7(2H, m); 7.6–7.8(1H, m); 7.2–7.4(1H, m); 6.86(4H, q); 5.14(1H, t); 4.26(2H, t); 3.84(1H, t); 2.2–2.8(2H, m); 1.92(4H, bt); 1.1–1.5(4H, m); 0.90(3H, bt) |
| 69 | 4-propoxyphenyl | " | " | " | δ: 8.5–8.7(2H, m); 7.6–7.8(1H, m); 7.2–7.4(1H, m); 6.98–7.15(2H, m); 6.5–7.7(3H, m); 3.80(2H, t); 2.2–2.85(4H, m); 1.4–2.1(6H, m); 0.8–1.1(6H, t+t) |
| 70 | 2-methoxy-phenyl | 3 | " | CH$_2$=CH—CH$_2$— | δ: 8.45–8.65(2H, m); 7.50–7.65(1H, m); 7.2–7.4(1H, m); 6.6–7.1(4H, m); 5.3–5.9(1H, m); 4.85–5.10(2H, q); 3.65(3H, s); 2.4–2.6(4H, m); 1.2–1.9(4H, m) |
| 71 | " | " | " | CH$_3$(CH$_2$)$_2$— | δ: 8.5–8.7(2H, m); 7.58–7.68(1H, m); 7.15–7.25(1H, m); 6.7–7.1(4H, m); 3.68(3H, s); 2.54(2H, t); 1.2–2.1(8H, m); 0.85–1.0(3H, bt) |
| 72 | 2-trifluoro-methylphenyl | 2 | CN | CH$_3$(CH$_2$)$_2$— | δ: 7.6–7.8(2H, m); 7.8–7.9(1H, m); 7.2–7.6(5H, m); 2.6–3.1(2H, m); 1.9–2.4(4H, m); 1.2–1.5(2H, m); 0.95(3H, bt) m.p. = 92–94° C. |
| 73 | " | " | " | CH$_3$(CH$_2$)$_3$— | δ: 8.6–8.8(2H, m); 7.6–7.7(1H, m); 7.1–7.5(5H, m); 2.6–3.1(2H, m); 1.8–2.4(4H, m); 1.1–1.5(4H, m); 0.85(3H, bt) |
| 74 | 2-fluorophenyl | " | " | " | δ: 8.6–8.8(2H, m); 7.7–7.9(1H, m); 7.2–7.4(1H, m); 6.8–7.1(4H, m); 2.5–2.8(2H, m); 1.8–2.4(4H, m); 1.1–1.4(4H, m); 0.95(3H, bt) |
| 75 | " | " | " | CH(CH$_2$)$_2$— | δ: 8.5–8.8(2H, m); 7.7–7.85(1H, m); 7.25–7.35(1H, m); 6.8–7.1(4H, m); 2.5–2.9(2H, m); 1.8–2.4(4H, m); 1.1–1.5(2H, m); 0.95(3H, bt) |
| 76 | 4-methoxyphenyl | 3 | " | CH$_3$(CH$_2$)$_3$— | δ: 8.5–8.7(2H, m); 7.6–7.75(1H, m); 7.1–7.3(1H, m); 6.84(4H, q); 3.80(3H, s); 2.50(2H, t); 1.6–2.1(4H, m); 1.1–1.5(6H, m); 0.85(3H, bt) |
| 77 | 4-fluorophenyl | 2 | CN | CF$_3$(CH$_2$)$_2$— | δ: 8.6–8.8(2H, m); 7.7–7.9(1H, m); 7.2–7.4(1H, m); 6.8–7.1(4H, m); 1.9–2.8(8H, m) |
| 78 | " | " | " | CF$_3$(CH$_2$)$_3$— | δ: 8.6–8.8(2H, m); 7.65–7.85(1H, m); 7.2–7.4(1H, m); 6.8–7.0(4H, m); 1.9–2.8(6H, m); 1.2–1.7(4H, m) |
| 79 | 4-methylphenyl | " | " | " | δ: 8.6–8.8(2H, m); 7.7–7.9(1H, m); 7.25–7.45(1H, m); 7.15(4H, s); 1.9–2.8(6H, m); 2.3(3H, s); 1.2—1.7(4H, m) |
| 80 | " | " | " | CF$_3$(CH$_2$)$_2$— | δ: 8.6–8.8(2H, m); 7.7–7.9(1H, m); 7.2–7.4(1H, m); 7.0(4H, s); 1.8–2.8(8H, m); 2.3(3H, s) |
| 81 | " | " | " | FCH$_2$(CH$_2$)$_2$— | δ: 8.5–8.7(2H, m); 7.6–7.8(1H, m); 7.2–7.4(1H, m); 7.0(4H, s); 4.75(1H, t); 3.95(1H, t); 1.9–3.1(8H, m); 2.2(3H, s) |
| A | phenyl | " | " | C$_6$H$_5$—(CH$_2$)$_2$— | δ: 2.22(2H, mCH$_2$); 2.69(2H, m, CH$_2$); 3.30(4H, m, CH$_2$); 7.24(10H, m, ArH); 8.19(1H, m, H$_5$); 8.69(1H, m, H$_4$); 9.07(1H, m, H$_6$); 9.18(1H, S, H$_2$) (300 MHz, DMSOd$_6$) |

TABLE I-continued

| B | 4-t-butylphenyl | 1 | " | 4-t-butyl-$C_6H_5$—$CH_2$— | δ: | 1.19(18H, S, $CH_3$); 3.41(4H, m, $CH_2$); 3.30(4H, m, $CH_2$); 7.24(10H, m, ArH); 8.19(1H, m, $H_5$); 8.69(1H, m, $H_4$); 9.07(1H, m, $H_5$); 9.18(1H, S, $H_2$) (300 MHz, $DMSOd_6$) |
|---|---|---|---|---|---|---|

*HCl salt log P Values

One determinant of the effectiveness of a fungicidal chemical is the ability of the chemical to penetrate plant or fungal tissue. The entry of a chemical into living tissue is controlled in large part by the lipophilicity of the chemical.

The lipophilicity of a chemical can be characterized by the ratio of its solubilities in octanol and water in a system equilibrated at or near room temperature. Because of the wide range of values that this ratio can assume, it is generally expressed on a logarithmic scale. The logarithm of the ratio of oil to water solubilities can be expressed as log P.

Measured values for log P have been reported in the chemical literature for over 10,000 different chemical substances. From these data it is possible to correlate log P with chemical structure by assigning incremental values of log P to various chemical substructures. As a result it is possible predict log P for unknown compounds or for compounds of unmeasured log P by the sum of the appropriate incremental values.

There are several microcomputer programs available for performing the calculation of log P based on chemical structure. These include, for example, CLOGP from Pomona College and CHEMCALC from the Tokyo Institute of Technology. For the purposes of this invention, a different computer program was devised to perform the log P calculations.

Each computer program can estimate log P for a variety of chemical structures with a standard deviation of about 0.25 $log_{10}$ unit from experimentally measured values. This error is about the same as the usual experimental error observed in measurements of log P.

To characterize the compounds of this invention by log P, a computer program was used to estimate values of log P for the groups $R(CH_2)_n$ and $R^1$ of the compound of formula I. This was done by estimating log P for the compounds $R(CH_2)_nH$ and $R^1H$, then subtracting 0.45 (the value for log P of a single hydrogen atom) from the log P of each to give log P values for the groups.

It was found that the compounds of this invention can be characterized as having sums of log P for $R(CH_2)_n$ and log P for $R^1$ in the range of about 4.6 to about 6.6. A more preferred range is from about 5.0 to about 6.2. The existence of a relatively broad range is not unusual because it is well known that a plot of biological activity as ordinate versus log P as abscissa commonly gives a parabolic curve which is convex upward. Accordingly, a useful range of biological activity can be found on either side of the log P value corresponding to maximum biological activity. At the same time, the existence of a limited range of log P as an indicator for useful biological activity permits using combinations of the log P values of $R(CH_2)_n$ and $R^1$ to help predict which compounds would be active and which compounds would not be active.

Use of calculated partition coefficients is known and has been used in practice. It has become customary to replace the actual measurement of partition coefficients by calculated or computed methods. Indication of such methods can be found in the "Handbook of Chemical Property Estimation Methods: Environmental Behavior of Organic Compounds" by Lyman, Reehl, and Rosenblatt, McGraw-Hill Book Company, 1982, and "Substituent Constants for Correlation Analysis in Chemistry and Biology", by Hansch and Leo, John Wiley & Sons, 1979.

Listed below in Table IA are the calculated log P values for the moieties $R(CH_2)_n$ and $R^1$, as well as the sums of these two values, for each of the compounds 1–81 (except 61 and 62) listed in Table I above. Tables II and III below, show that there is good correlation between the most biologically active compounds and the preferred ranges of sums of log P values.

TABLE 1A log P Values

| Compound No. | log P $R(CH_2)_n$ | log P $R^1$ | Sum of log P Values |
|---|---|---|---|
| 1 | 2.69 | 1.75 | 4.44 |
| 2 | 2.69 | 3.95 | 4.64 |
| 3 | 2.69 | 2.85 | 5.54 |
| 4 | 2.69 | 0.32 | 3.01 |
| 5 | 2.69 | 1.28 | 3.97 |
| 6 | 2.69 | −0.65 | 2.04 |
| 7 | 2.69 | 2.16 | 4.85 |
| 8 | 2.69 | 2.38 | 5.07 |
| 9 | 3.37 | 1.28 | 4.65 |
| 10 | 3.37 | 1.75 | 5.12 |
| 11 | 3.37 | 2.30 | 5.67 |
| 12 | 3.82 | 1.75 | 5.57 |
| 13 | 3.82 | 2.30 | 6.12 |
| 14 | 4.06 | 1.75 | 5.81 |
| 15 | 4.82 | 1.75 | 6.57 |
| 16 | 4.06 | 3.40 | 7.46 |
| 17 | 4.76 | 1.28 | 6.04 |
| 18 | 4.06 | 1.28 | 5.34 |
| 19 | 4.06 | 2.30 | 6.36 |
| 20 | 2.45 | 1.75 | 4.20 |
| 21 | 2.45 | 2.30 | 4.75 |
| 22 | 2.45 | 1.28 | 3.73 |
| 23 | 2.45 | 3.95 | 6.40 |
| 24 | 2.45 | 2.38 | 4.83 |
| 25 | 2.69 | 1.75 | 4.44 |
| 26 | 2.69 | 2.30 | 4.99 |
| 27 | 3.72 | 2.30 | 6.02 |
| 28 | 3.72 | 1.28 | 5.00 |
| 29 | 3.72 | 2.16 | 5.88 |
| 30 | 3.72 | 2.85 | 6.57 |
| 31 | 3.72 | 2.30 | 6.02 |
| 32 | 3.82 | 1.76 | 5.58 |
| 33 | 3.24 | 1.28 | 4.52 |
| 34 | 3.24 | 2.30 | 5.54 |
| 35 | 3.14 | 2.30 | 5.44 |
| 36 | 3.72 | 3.40 | 7.12 |
| 37 | 3.72 | 1.76 | 5.48 |
| 38 | 3.72 | 0.32 | 4.04 |
| 39 | 3.37 | 2.16 | 5.53 |
| 40 | 3.14 | 1.28 | 4.42 |
| 41 | 3.37 | 0.32 | 3.69 |
| 42 | 3.14 | 2.30 | 5.44* HCl Salt |

TABLE 1A-continued log P Values

| Compound No. | log P R(CH$_2$)$_n$ | log P R$^1$ | Sum of log P Values |
|---|---|---|---|
| 43 | 3.14 | 2.16 | 5.30 |
| 44 | 3.14 | 3.40 | 6.54 |
| 45 | 3.37 | 3.40 | 6.77 |
| 46 | 3.14 | 1.75 | 4.89 |
| 47 | 3.37 | 2.38 | 5.75 |
| 48 | 3.72 | 2.38 | 6.10 |
| 49 | 3.37 | 2.71 | 6.08 |
| 50 | 3.72 | −0.65 | 3.07 |
| 51 | 3.37 | −0.65 | 2.62 |
| 52 | 3.37 | — | — |
| 53 | 3.37 | 0.25 | 3.62 |
| 54 | 4.24 | 2.30 | 6.54 |
| 55 | 3.37 | 2.71 | 6.08 |
| 56 | 4.24 | 1.28 | 5.52 |
| 57 | 4.24 | 1.75 | 5.99 |
| 58 | 4.24 | 2.06 | 6.40 |
| 59 | 3.37 | 1.83 | 5.20 |
| 60 | 3.37 | 2.85 | 6.22 |
| 61 | — | — | — |
| 62 | — | — | — |
| 63 | 4.27 | 2.44 | 6.71 |
| 64 | 3.37 | 0.80 | 4.17 |
| 65 | 3.37 | 1.86 | 5.23 |
| 66 | 2.92 | 0.80 | 3.72 |
| 67 | 2.92 | 1.28 | 4.20 |
| 68 | 2.19 | 2.30 | 4.49 |
| 69 | 3.69 | 1.75 | 5.44 |
| 70 | 3.14 | 1.28 | 4.42 |
| 71 | 3.14 | 1.75 | 4.89 |
| 72 | 3.76 | 1.75 | 5.51 |
| 73 | 3.76 | 2.30 | 6.06 |
| 74 | 2.92 | 2.30 | 5.22 |
| 75 | 2.92 | 1.75 | 4.67 |
| 76 | 3.14 | 2.30 | 5.44 |
| 77 | 2.82 | 2.20 | 5.02 |
| 78 | 2.82 | 2.75 | 5.57 |
| 79 | 3.14 | 2.75 | 5.89 |
| 80 | 3.14 | 2.20 | 5.34 |
| 81 | 3.14 | 0.70 | 3.84 |

EXAMPLE 9
Preparation of Fungicidal Compositions

Compositions containing Compounds Nos. 1–81 were prepared by dissolving 0.24 grams of each of the compounds in 8 ml of acetone or other suitable inert solvent. Each of the resultant solutions was treated with 3 drops of TWEEN 20 (ethoxylated ethylene sorbitan monolaurate, a non-ionic surfactant)(I.C.I.), and water was added to form an emulsion. The degree of dilution with water was dictated by the desired concentration of the compound in the composition. The greater the quantity of water added, the lower the concentration of the compound in the composition, reported in milligrams per liter (mg/l)

EXAMPLE 10
Control of Cucumber and Barley Powdery Mildew Fungus (Systemic Root Uptake)

Each of the Compounds Nos. 1–81 was tested to evaluate its effectiveness in preventing or controlling powdery mildew disease of barley caused by the fungus *Erysiphe graminis* and powdery mildew disease of cucumber caused by the fungus, *Erysiphe cichoracearum*, by systemic root uptake.

A plurality of pots (4×4×3.5 inches) each containing 10 plants of barley (Variety "Robust") and cucumber (Variety "Marketmore 76") were grown to age 6 days and 10 days, respectively. Upon reaching these ages, the plants were either treated with 45 ml of 250 mg/l concentration of the compositions of Example 9 or were left untreated. The untreated plants were used as controls. The 45 ml compositions saturated the soil of the treated pots without significant loss through drainage into the saucers below the pots.

Twenty-four hours after the treatment with the compositions, both the barley and cucumber plants in all the pots, those treated and those untreated, were inoculated with powdery mildew fungus. This was accomplished by tapping leaves of previously infected barley and cucumber plants over the treated and untreated pots containing the barley and cucumber plants, respectively, to distribute spores of the fungus over the plants tested.

Eight days after inoculation, disease control was evaluated on a 0 to 6 rating scale. A 0 rating was assigned when no disease was evidenced and a 6 rating was given for severe disease. Intermediate ratings were assigned depending on the degree of disease. Percent control was computed by comparing the ratings for the treated and untreated plants on this 0 to 6 scale. The results are reported in Table II below. The results of the powdery mildew disease control of barley are reported under the heading of "BMS". The results for cucumber mildew control are reported under the heading "CMS".

EXAMPLE 11
Control of Powdery Mildew in Barley by Foliar Application

Ten plants of "Robust" variety barley were planted in each of a plurality of pots.

Each pot was then either sprayed with one of the compositions of Example 9, at a composition concentration of 1,000 mg/l, or left unsprayed. For each pot sprayed, one pot was left unsprayed as a control.

After the leaves of the sprayed pots were dried, the sprayed pots and the unsprayed control pots were placed in a greenhouse maintained at 21° C. All the pots were then inoculated with barley powdery mildew fungus, *Erysiphe graminis*. This inoculation was accomplished by distributing spores of the fungus over the leaves of the plants to be tested from plants which had previously been infected with the mildew disease.

Eight days after inoculation, the plants were evaluated and assigned a disease rating of 0 to 6 as described in Example 10. Again, percent control was computed by comparing the treatment scores with the scores of the untreated controls. The results are summarized in Table II under the heading "ERY GRA".

Using a similar procedure as described above for the barley, pinto bean plants were prepared, treated and inoculated with the fungus *Erysiphe polygoni*. The results of this testing are summarized in Table II under the heading "ERY POL".

EXAMPLE 12
Control of Rice Blast Disease by Foliar Treatment

Five "Leger" or "Rodeo" barley plants were grown in each of a plurality of pots.

Six days after planting, each of the barley plants was then either sprayed with one of the compositions of Example 9, at a concentration of 1,000 mg/l, or left unsprayed. An equal number of pots were sprayed and unsprayed.

Sprayed and unsprayed pots were then inoculated with spores of the rice blast fungus, *Pyricularia oryzae*. This inoculation was accomplished by preparing inoculum containing 20,000 to 30,000 spores per milliliter. The inoculum so prepared was sprayed on the plants with 1 to 2 drops of TWEEN 20 (ethoxylated ethylene sorbitan monolaurate) (ICI), a non-ionic surfactant, to insure proper wetting of the inoculum onto the plant leaves.

The plants were incubated in a controlled chamber at a humidity of 99% and a temperature of 21° C. to allow infection to occur. After 48 hours in the chamber, the plants were transferred to a greenhouse for seven days to permit disease development to occur. Disease was manifested by blast lesions on the leaves. Disease control of the sprayed plants and the control plants, was calculated by either counting lesions, if infection was moderate, or evaluation by the 0 to 6 rating system defined in Example 10. These results are summarized in Table II under the heading "PYR ORY".

EXAMPLE 13
Control of Bean Rust Fungus Eradicant Test

A plurality of pots were each planted with two pinto bean plants, Phaseolus vulgaris, each, susceptible to rust disease. When the plants were 7 days old, at the primary leaf stage of growth, they were all sprayed with a suspension containing 20,000 spores of the bean rust fungus, Uromyces phaseoli, per ml. All the pots were then incubated in a controlled environmental chamber, maintained at 99% humidity and 21° C., for 24 hours to allow infection to occur. The plants were then removed from the incubator and allowed to dry. Two days after inoculation each of the infected plants was then either sprayed with one of the compositions of Example 9, at a dosage of 1,000 mg/l, or left unsprayed. The unsprayed plants acted as controls. All of the sprayed and unsprayed plants were then placed in a greenhouse at 21° C. for nine days to allow the disease to develop.

The plants sprayed with the spore suspension were assessed for disease using the 0 to 6 rating system described in Example 10. Control of disease was determined by comparing treated plants with the untreated controls. The results, expressed as percent reduction of disease, are summarized in Table II under the heading "URO PHA".

EXAMPLE 14
Control of Barley Spot Blotch by Foliar Treatment

Ten plants of six day-old Barley (variety "Robust") were planted in each of a plurality of pots. Each pot was then either sprayed with one of the compositions of Example 9, at a concentration of 1,000 mg/l, or left unsprayed. The unsprayed plants were used as controls. An equal number of pots were sprayed and unsprayed.

All plants, sprayed and unsprayed, were thereafter inoculated with spores of the blotch fungus Helminthosporium sativum. All inoculated plants were placed in a 99% humidity chamber for 24 hours and then placed in a greenhouse, maintained at a temperature of 21° C., for eight days. After that time, the plants were evaluated using the "0 to 6" disease-rating system described in Example 10.

Percent control was computed and the results are summarized in Table II under the heading "HEL SAT".

EXAMPLE 15
Control of Eight Fungus Species

Compounds listed in Table I were solubilized in acetone at a concentration of 500 mg/l such that there were 500 parts by weight of active compound per million parts by volume of acetone. Filter paper discs, each 11 mm. in diameter, were dipped in each of the test solutions. The discs were allowed to air dry to drive off the acetone solvent. A number of untreated discs were used as controls.

The treated and untreated discs were then placed on agar plates and one of the following fungus species: Septoria nodorum (SEP NOD), Botrytis cinerea (BOT CIN), Fusarium oxysporum (FUS OXY), Pythium ultimum (PYT ULT), Rhizoctonia solani (RHI SOL), Colletotrichum gossypii (COL GOS), and Sclerotinia minor (SCL MIN), was added to the center of each disc in the form of a culture plug with the fungus mat in contact with the paper of the test disc. Cercosporidium personatum (CER PER), was added to discs as a spore suspension (20,000 spores/ml) to the disc (two drops of spore suspension per disc), rather than a mycelial culture plug. The plates were then incubated at 29° C. in an oven.

With the exception of the discs containing Cercosporidium personatum, the discs were evaluated by first measuring the radius from the center of the fungus colony on the treated discs and on the untreated discs. Percent growth inhibition of each of the compounds tested was determined as a function of the difference between the radius of the fungus colony on the treated disc versus the radius of the fungus colony on the untreated disc.

In the case of the Cercosporidium personatum (CER PER) fungi, scoring was done on a numerical basis as follows:

100=Complete inhibition of germination and growth.

80=Nearly complete inhibition but some growth.

50=Partial inhibition of growth or, early complete inhibition but later growth begins.

20=Some inhibition of growth, but not significant.

0=No inhibition of growth.

The results of all the above tests appear in Table III below under the headings "SEP NOD," "BOT CIN," "FUS OXY," "PYT ULT," "SCL MIN," "RHI SOL" "COL GOS" and "CER PER".

TABLE II

FUNGICIDAL ACTIVITY
(Percent Reduction of Disease)

| CMPD No. | BMS | CMS | URO PHA | ERY POL | ERY GRA | PYR ORY | HEL SAT |
|---|---|---|---|---|---|---|---|
| 1 | 60 | 0 | 60 | 95 | 100 | 0 | 65 |
| 2 | 0 | 0 | 97 | 100 | 100 | 45 | 80 |
| 3 | 35 | 35 | 100 | 100 | 100 | 100 | 100 |
| 4 | 35 | 20 | 0 | 90 | 70 | 50 | 0 |
| 5 | 85 | 88 | 90 | 90 | 85 | 83 | 70 |
| 6 | 100 | 100 | 50 | 100 | 70 | 0 | 100 |
| 7 | 35 | 20 | 90 | 100 | 100 | 83 | 70 |
| 8 | 45 | 0 | 80 | 99 | 100 | 0 | 100 |
| 9 | 40 | 74 | 100 | 99 | 100 | 70 | 85 |
| 10 | 84 | 88 | 100 | 99 | 100 | 70 | 100 |
| 11 | 74 | 39 | 100 | 100 | 100 | 85 | 100 |
| 12 | 40 | 40 | 100 | 95 | 100 | 85 | 100 |
| 13 | 40 | 0 | 100 | 100 | 100 | 85 | 100 |
| 14 | 0 | 84 | 33 | 100 | 100 | 100 | 60 |
| 15 | 0 | 96 | 83 | 100 | 100 | 85 | 100 |
| 16 | 0 | 0 | 0 | 100 | 85 | 20 | 85 |
| 17 | 0 | 100 | 0 | 100 | 70 | 70 | 0 |
| 18 | 20 | 20 | 0 | 100 | 100 | 85 | 100 |
| 19 | 35 | 0 | 0 | 100 | 100 | 35 | 100 |
| 20 | 63 | 40 | 0 | 100 | 90 | 50 | 80 |
| 21 | 0 | 20 | 0 | 0 | 0 | 0 | 0 |
| 22 | 35 | 0 | 0 | 0 | 70 | 0 | 0 |
| 23 | 0 | 20 | 0 | 0 | 50 | 20 | 0 |
| 24 | 0 | 0 | 0 | 0 | 50 | 0 | 0 |
| 25 | 0 | 17 | 17 | 17 | 67 | 0 | 0 |
| 26 | 0 | 0 | 0 | 17 | 50 | 0 | 0 |
| 27 | 0 | 0 | 100 | 90 | 90 | 70 | 90 |
| 28 | 0 | 0 | 100 | 100 | 90 | 85 | 100 |
| 29 | 0 | 0 | 100 | 100 | 100 | 85 | 100 |
| 30 | 0 | 0 | 100 | 100 | 100 | 100 | 90 |
| 31 | 0 | 0 | 35 | 90 | 20 | 0 | 90 |
| 32 | 0 | 0 | 85 | 100 | 100 | 100 | 90 |
| 33 | 40 | 20 | 100 | 100 | 100 | 85 | 100 |
| 34 | 0 | 20 | 100 | 100 | 100 | 0 | 100 |
| 35 | 0 | 0 | 90 | 100 | 85 | 55 | 100 |
| 36 | 0 | 0 | 100 | 100 | 85 | 90 | 100 |

TABLE II-continued

FUNGICIDAL ACTIVITY
(Percent Reduction of Disease)

| CMPD No. | BMS | CMS | URO PHA | ERY POL | ERY GRA | PYR ORY | HEL SAT |
|---|---|---|---|---|---|---|---|
| 37 | 0 | 0 | 92 | 92 | 92 | 100 | 100 |
| 38 | 0 | 0 | 0 | 92 | 83 | 17 | 100 |
| 39 | 0 | 0 | 92 | 92 | 92 | 100 | 100 |
| 40 | 0 | 0 | 17 | 92 | 67 | 92 | 100 |
| 41 | 0 | 0 | 0 | 100 | 92 | 92 | 100 |
| 42 | 0 | 0 | 33 | 100 | 92 | 67 | 100 |
| 43 | 0 | 0 | 83 | 92 | 92 | 100 | 100 |
| 44 | 0 | 0 | 92 | 90 | 83 | 17 | 100 |
| 45 | 0 | 67 | 92 | 90 | 92 | 17 | 100 |
| 46 | 0 | 0 | 33 | 90 | 92 | 0 | 100 |
| 47 | 0 | 0 | 33 | 90 | 70 | 0 | 100 |
| 48 | 0 | 0 | 83 | 90 | 67 | 33 | 100 |
| 49 | 0 | 0 | 83 | 90 | 100 | 17 | 100 |
| 50 | 0 | 0 | 90 | 100 | 80 | 0 | 100 |
| 51 | 90 | 0 | 20 | 85 | 91 | 20 | 90 |
| 52 | 100 | 85 | 70 | 100 | 100 | 90 | 100 |
| 53 | 100 | 0 | 0 | 90 | 100 | 70 | 90 |
| 54 | 0 | 0 | 35 | 90 | 100 | 90 | 100 |
| 55 | 75 | 0 | 0 | 85 | 100 | 70 | 90 |
| 56 | 0 | 0 | 0 | 90 | 90 | 90 | 100 |
| 57 | 0 | 0 | 0 | 90 | 90 | 100 | 100 |
| 58 | 0 | 0 | 0 | 85 | 90 | 85 | 0 |
| 59 | 75 | 0 | 35 | 90 | 100 | 85 | 90 |
| 60 | 75 | 0 | 50 | 90 | 100 | 70 | 90 |
| 61 | 20 | 40 | 0 | 100 | 100 | 50 | 85 |
| 62 | 20 | 20 | 35 | 100 | 0 | 0 | 0 |
| 63 | 0 | 0 | 0 | 100 | 0 | 0 | 0 |
| 64 | 20 | 0 | 70 | 100 | 0 | 20 | 85 |
| 65 | 0 | 0 | 50 | 100 | 85 | — | 100 |
| 66 | 100 | 40 | 70 | 100 | 50 | 0 | 100 |
| 67 | 100 | 20 | 50 | 100 | 100 | 0 | 100 |
| 68 | 0 | 0 | 50 | 100 | 75 | 70 | 100 |
| 69 | 0 | 20 | 0 | 100 | 50 | 0 | 85 |
| 70 | 40 | 0 | 17 | 92 | 92 | 0 | 100 |
| 71 | 100 | 80 | 92 | 100 | 100 | 0 | 100 |
| 72 | 90 | 80 | 0 | 92 | 100 | 0 | 83 |
| 73 | 100 | 0 | 100 | 100 | 100 | 0 | 100 |
| 74 | 100 | 80 | 92 | 100 | 100 | 0 | 100 |
| 75 | 100 | 0 | 83 | 100 | 92 | 0 | 92 |
| 76 | 0 | 0 | 67 | 100 | 100 | 0 | 100 |
| 77 | 100 | 100 | 90 | 100 | 90 | 35 | 90 |
| 78 | 100 | 92 | 83 | 92 | 100 | 100 | 83 |
| 79 | 92 | 92 | 0 | 100 | 100 | 11 | 100 |
| 80 | 100 | 92 | 83 | 100 | 100 | 78 | 100 |
| 81 | 0 | 0 | 90 | 100 | 70 | — | — |
| A | 15 | 50 | 0 | 15 | 0 | 10 | 60 |
| B | 10 | 50 | 0 | 0 | 15 | — | 0 |

TABLE III

FUNGICIDAL ACTIVITY
(Percent Growth Inhibition)

| CMPD No. | SEP NOD | CER PER | PYT ULT | SCL MIN | RHI SOL | BOT CIN | FUS OXY | COL GOS |
|---|---|---|---|---|---|---|---|---|
| 1 | 0 | 100 | 40 | 100 | 95 | 5 | 97 | 100 |
| 2 | 0 | 100 | 0 | 100 | 0 | 60 | 30 | 60 |
| 3 | 86 | 100 | 5 | 100 | 10 | 100 | 0 | 97 |
| 4 | 92 | 100 | 100 | 98 | 82 | 94 | 100 | 100 |
| 5 | 50 | 0 | 82 | 95 | 100 | 100 | 76 | 97 |
| 6 | 0 | 0 | 50 | 100 | 50 | 100 | 93 | 95 |
| 7 | 5 | 0 | 35 | 10 | 94 | 100 | 100 | 89 |
| 8 | 25 | 80 | 35 | 100 | 45 | 40 | 0 | 95 |
| 9 | 30 | 100 | 35 | 98 | 95 | 100 | 100 | 100 |
| 10 | 80 | 100 | 40 | 100 | 96 | 98 | 97 | 97 |
| 11 | 60 | 0 | 40 | 98 | 98 | 100 | 10 | 100 |
| 12 | 70 | 100 | 90 | 92 | 98 | 98 | 80 | 93 |
| 13 | 75 | 0 | 10 | 94 | 100 | 98 | 60 | 93 |
| 14 | 0 | 0 | 10 | 5 | 5 | 15 | 25 | 5 |
| 15 | 93 | 100 | 83 | 100 | 98 | 30 | 95 | 93 |
| 16 | 45 | 0 | 45 | 5 | 25 | 20 | 5 | 42 |
| 17 | 55 | 0 | 45 | 10 | 45 | 5 | 60 | 20 |
| 18 | 5 | 0 | 40 | 10 | 40 | 10 | 50 | 10 |
| 19 | 96 | 100 | 93 | 100 | 91 | 40 | 100 | 91 |
| 20 | 70 | 100 | 88 | 100 | 90 | 30 | 100 | 92 |
| 21 | 91 | 50 | 93 | 95 | 5 | 60 | 86 | 85 |
| 22 | 0 | 0 | 83 | 100 | 55 | 35 | 0 | 15 |
| 23 | 79 | 100 | 93 | 98 | 60 | 65 | 100 | 87 |
| 24 | 90 | 100 | 80 | 93 | 60 | 60 | 97 | 80 |
| 25 | 19 | 0 | 0 | 86 | 4 | 55 | 63 | 72 |
| 26 | 45 | 0 | 0 | 96 | 4 | 5 | 59 | 75 |
| 27 | 10 | — | 10 | 93 | 5 | 78 | 10 | 20 |
| 28 | 96 | 100 | 10 | 96 | 60 | 98 | 100 | 100 |
| 29 | 83 | 100 | 0 | 94 | 70 | 98 | 97 | 95 |
| 30 | 96 | 0 | 0 | 100 | 10 | 88 | 100 | 80 |
| 31 | 81 | 0 | 93 | 75 | 5 | 89 | 83 | 70 |
| 32 | 89 | 0 | 0 | 98 | 0 | 96 | 100 | 97 |
| 33 | 96 | 0 | 50 | 100 | 0 | 98 | 100 | 100 |
| 34 | 100 | 0 | 0 | 100 | — | 100 | 100 | 100 |
| 35 | 90 | 0 | 0 | 88 | 40 | 91 | 30 | 97 |
| 36 | 96 | 0 | 75 | 100 | 25 | 45 | 80 | 0 |
| 37 | 100 | 0 | 9 | 100 | 13 | 100 | 100 | 100 |
| 38 | 100 | 0 | 100 | 46 | 0 | 100 | 100 | 100 |
| 39 | 8 | 0 | 44 | 42 | 11 | 57 | 30 | 75 |
| 40 | 100 | 0 | 61 | 100 | 0 | 100 | 100 | 100 |
| 41 | 63 | 0 | 9 | 48 | 26 | 32 | 30 | 100 |
| 42 | 100 | 0 | 3 | 44 | 32 | 100 | 100 | 100 |
| 43 | 100 | 100 | 36 | 100 | 48 | 100 | 100 | 94 |
| 44 | 100 | 100 | 89 | 100 | 30 | 43 | 8 | 100 |
| 45 | 100 | 100 | 89 | 100 | 6 | 100 | 14 | 100 |
| 46 | 100 | 0 | 59 | 100 | 8 | 100 | 100 | 100 |
| 47 | 100 | 0 | 100 | 100 | 45 | 100 | 50 | 100 |
| 48 | 100 | 50 | 53 | 100 | 28 | 100 | 100 | 100 |
| 49 | 100 | 0 | 76 | 100 | 100 | 100 | 65 | 100 |
| 50 | 100 | 0 | 10 | 100 | 20 | 0 | 100 | 100 |
| 51 | 100 | 100 | 0 | 100 | 30 | 100 | 100 | 100 |
| 52 | 100 | 100 | 0 | 100 | 100 | 100 | 100 | 100 |
| 53 | 100 | 0 | 5 | 100 | 75 | 100 | 100 | 100 |
| 54 | 100 | 0 | 5 | 100 | 100 | 100 | 100 | 100 |
| 55 | 10 | 0 | 20 | 55 | 50 | 40 | 65 | 30 |
| 56 | 40 | 0 | 5 | 45 | 45 | 100 | 60 | 35 |
| 57 | 40 | 0 | 5 | 65 | 40 | 30 | 55 | 15 |
| 58 | 70 | 0 | 0 | 75 | 5 | 10 | 40 | 15 |
| 59 | 100 | 0 | 5 | 70 | 5 | 100 | 100 | 100 |
| 60 | 100 | 0 | 50 | 100 | 100 | 100 | 20 | 30 |
| 61 | 20 | 100 | 100 | 100 | 80 | 100 | 100 | 100 |
| 62 | 0 | 0 | 5 | 100 | 5 | 0 | 10 | 25 |
| 63 | 100 | 0 | 10 | 100 | 5 | 40 | 20 | 25 |
| 64 | 100 | 0 | 0 | 50 | 20 | 100 | 100 | 55 |
| 65 | 100 | 0 | 100 | 100 | 30 | 100 | 100 | 100 |
| 66 | 100 | 0 | 0 | 100 | 45 | 100 | 100 | 100 |
| 67 | 100 | 100 | 20 | 100 | 40 | 100 | 100 | 100 |
| 68 | 100 | 100 | 40 | 100 | 45 | 100 | 100 | 100 |
| 69 | 100 | 0 | 35 | 100 | 5 | 70 | 30 | 100 |
| 70 | 100 | 100 | 49 | 100 | 28 | 100 | 25 | 100 |
| 71 | 100 | 100 | 60 | 100 | 6 | 100 | 72 | 100 |
| 72 | 100 | 0 | 71 | 100 | 38 | 100 | 16 | 100 |
| 73 | 70 | 0 | 69 | 100 | 34 | 100 | 75 | 85 |
| 74 | 100 | 0 | 36 | 100 | 100 | 100 | 3 | 100 |
| 75 | 100 | 0 | 1 | 92 | 100 | 100 | 100 | 100 |
| 76 | 100 | 100 | 0 | 100 | 6 | 100 | 50 | 100 |
| 77 | 20 | 0 | 30 | 40 | 40 | 65 | 55 | 15 |
| 78 | 30 | 0 | 0 | 20 | 0 | 34 | 40 | 50 |
| 79 | 30 | 0 | 0 | 5 | 35 | 0 | 46 | 30 |
| 80 | 0 | 0 | 7 | 5 | 62 | 9 | 24 | 59 |
| 81 | 40 | 0 | 20 | 0 | 5 | 30 | 20 | 20 |
| A | 0 | 0 | 10 | 10 | 10 | 0 | 10 | 25 |
| B | 10 | 0 | 15 | 60 | 15 | 0 | 0 | 0 |

Unlike the compounds of this invention (which have four different distinct groups attached to the tetrahedral center carbon atom), Comparative Compounds A and B have two identical groups attached to the tetrahedral center carbon atom, i.e.,

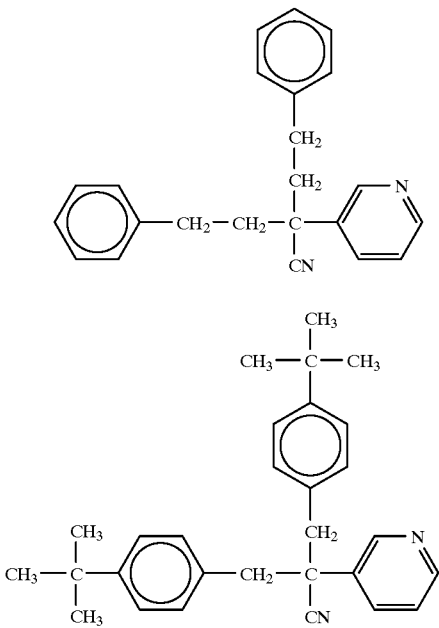

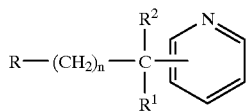

As can be seen from the results above, compared to Comparative Compounds A and B, the compounds of this invention have surprisingly superior activity.

What is claimed is:

1. A compound of the formula

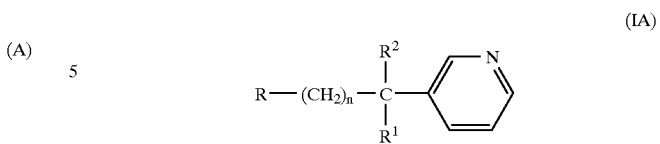

wherein R is a $C_6$–$C_{10}$ aryl group, optionally substituted with one or more halogen atoms, phenoxy, or, linear or branched, $C_1$–$C_6$ alkyl, $C_1$–$C_6$ alkoxy, $C_1$–$C_6$ haloalkoxy or $C_1$–$C_6$ haloalkyl; $R^1$ is $C_3$–$C_6$ cycloalkyl or, linear or branched, $C_1$–$C_6$ alkyl, $C_2$–$C_6$ alkenyl, $C_2$–$C_6$ alkynyl, $C_3$–$C_6$ haloalkenyl, $C_2$–$C_8$ alkoxyalkyl or $C_1$–$C_6$ haloalkyl; n is 1, 2 or 3; and $R^2$ is CN, C(O)NH$_2$ or C(S)NH$_2$, or the physiologically acceptable salts thereof with organic and inorganic acids.

2. A compound of the formula (IA)

wherein R is a $C_6$–$C_{10}$ aryl group, optionally substituted with one or more halogen atoms, phenoxy, or, linear or branched, $C_1$–$C_6$ alkyl, $C_1$–$C_6$ alkoxy, $C_1$–$C_6$ haloalkoxy or $C_1$–$C_6$ haloalkyl; $R^1$ is $C_3$–$C_6$ cycloalkyl or, linear or branched, $C_1$–$C_6$ alkyl, $C_2$–$C_6$ alkenyl, $C_2$–$C_6$ alkynyl, $C_3$–$C_6$ haloalkenyl, $C_2$–$C_8$ alkoxyalkyl or $C_1$–$C_6$ haloalkyl; n is 2 or 3; and $R^2$ is CN, C(O)NH$_2$ or C(S) NH$_2$, or the physiologically acceptable salts thereof with organic and inorganic acids.

3. A compound as recited in claim 2 wherein R is naphthyl or phenyl optionally substituted with one or more halogen atoms or, linear or branched, $C_1$–$C_4$ alkyl, $C_1$–$C_4$ alkoxy or $C_1$–$C_4$ haloalkoxy.

4. A compound as recited in claim 3 wherein R is phenyl optionally substituted with one or more halogen atoms or, linear or branched, $C_1$–$C_4$ alkyl, $C_1$–$C_4$ alkoxy or $C_1$–$C_4$ haloalkoxy.

5. A compound as recited in claim 2 wherein $R^1$ is $C_3$–$C_6$ cycloalkyl or, linear or branched, $C_2$–$C_4$ alkyl, $C_2$–$C_4$ haloalkyl, $C_2$–$C_4$ alkenyl or $C_2$–$C_4$ alkynyl.

6. A compound as recited in claim 2 wherein $R^2$ is a cyano group.

7. A compound as recited in claim 2 wherein R is naphthyl or phenyl optionally substituted with one or more halogen atoms or, linear or branched, $C_1$–$C_4$ alkyl, $C_1$–$C_4$ alkoxy or $C_1$–$C_4$ haloalkoxy; $R^1$ is $C_3$–$C_6$ cycloalkyl or, linear or branched, $C_2$–$C_4$ alkyl, $C_2$–$C_4$ haloalkyl, $C_2$–$C_4$ alkenyl or $C_2$–$C_4$ alkynyl; $R^2$ is a cyano group; and n is 2 or 3.

8. A compound as recited in claim 7 wherein R is phenyl optionally substituted with one or more halogen atoms or, linear or branched, $C_1$–$C_4$ alkyl, $C_1$–$C_4$ alkoxy or $C_1$–$C_4$ haloalkoxy.

9. A fungicidal composition comprising:
(a) a fungicidally effective amount of a compound of claim 1; and
(b) a suitable carrier.

10. A fungicidal composition comprising:
(a) a fungicidally effective amount of a compound of claim 2; and
(b) a suitable carrier.

11. A method for controlling undesirable fungi at a loci to be protected, which comprises applying a fungicidally effective amount of a compound as recited in claim 1 to the loci to be protected.

12. A method for controlling undesirable fungi at a loci to be protected, which comprises applying a fungicidally effective amount of a compound as recited in claim 2 to the loci to be protected.

* * * * *